United States Patent
Coley et al.

(10) Patent No.: US 6,585,663 B1
(45) Date of Patent: *Jul. 1, 2003

(54) ADVISORY METHOD

(75) Inventors: John Coley, Stanwick (GB); Paul J Davis, Felmersham (GB); Stephanie J Senior, Bromham (GB)

(73) Assignee: Inverness Medical Switzerland GmbH, Zug (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/905,171

(22) Filed: Aug. 1, 1997

Related U.S. Application Data (63) Continuation of application No. 08/458,184, filed on Jun. 2, 1995, now abandoned, which is a continuation of application No. 08/109,502, filed on Aug. 20, 1993, now abandoned.

(30) Foreign Application Priority Data

Aug. 21, 1992 (GB) .............................................. 9217808

(51) Int. Cl.$^7$ ................................................. A61B 5/00
(52) U.S. Cl. ......................... 600/551; 600/300; 600/345
(58) Field of Search ................................ 600/345, 551, 600/300

(56) References Cited

U.S. PATENT DOCUMENTS

| | | |
|---|---|---|
| 3,141,740 A | 7/1964 | Wild |
| 3,406,015 A | 10/1968 | Foster |
| 3,406,016 A | 10/1968 | Foster et al. |
| 3,434,801 A | 3/1969 | Scherr |
| 3,436,186 A | 4/1969 | Mcsweeney et al. |
| 3,749,089 A | 7/1973 | Derr |
| 3,875,013 A | 4/1975 | Manautou et al. |
| 3,924,609 A | 12/1975 | Friedenberg et al. |
| 3,926,037 A | 12/1975 | Kopito et al. |
| 3,968,011 A | 7/1976 | Manautou et al. |
| 3,986,494 A * | 10/1976 | Preti et al. .................. 128/738 |
| 3,991,174 A | 11/1976 | Grundman |
| 4,002,056 A | 1/1977 | Kopito et al. |
| 4,010,738 A | 3/1977 | Preti et al. |
| 4,013,066 A | 3/1977 | Schuster |
| 4,031,365 A | 6/1977 | Raggiotti et al. |
| 4,036,212 A | 7/1977 | Karuhn |
| 4,059,986 A | 11/1977 | Schuster |
| 4,072,045 A | 2/1978 | Kopito |
| 4,119,089 A | 10/1978 | Preti et al. |

(List continued on next page.)

FOREIGN PATENT DOCUMENTS

| | | |
|---|---|---|
| CA | 1 048 001 | 2/1979 |
| CA | 1 183 080 | 2/1985 |
| DE | 1 214 438 | 4/1966 |

(List continued on next page.)

OTHER PUBLICATIONS

Billings et al., "Symptoms and Hormonal Changes Accompanying Ovulation", *The Lancet*; Feb. 5, 1972; pp. 282–284 128/738.*

(List continued on next page.)

Primary Examiner—Robert L. Nasser
(74) Attorney, Agent, or Firm—Oppedahl & Larson, LLP (57) ABSTRACT

A method and test kit for providing contraceptive advice during the human ovulation cycle, involving simply the measurement of urinary lutenising hormone (LH) concentration on a daily basis during the early phase of the cycle until the LH surge indicative of ovulation is detected, together with calender means to advise the user to abstain from unprotected intercourse during a time interval commencing not later than a predetermined first day of LH testing and ending at least 2 days following the day of LH surge detection.

15 Claims, 5 Drawing Sheets

U.S. PATENT DOCUMENTS

| | | | |
|---|---|---|---|
| 4,123,510 A | 10/1978 | Banik et al. | |
| 4,148,304 A | 4/1979 | Mull | |
| 4,151,831 A | 5/1979 | Lester | |
| 4,151,833 A | 5/1979 | Polishuk | |
| 4,208,187 A | 6/1980 | Givner | |
| 4,232,215 A | 11/1980 | Hanley | |
| 4,246,907 A | 1/1981 | Bullock | |
| 4,261,371 A | 4/1981 | Reading, III | |
| 4,312,360 A | 1/1982 | Conway et al. | |
| 4,367,527 A | 1/1983 | Desjacques | |
| 4,370,727 A | 1/1983 | Bellet | |
| 4,377,171 A | 3/1983 | Wada | |
| 4,381,121 A | 4/1983 | Hanley | |
| 4,385,125 A | 5/1983 | Preti et al. | |
| 4,396,020 A | 8/1983 | Wolff et al. | |
| 4,408,905 A | 10/1983 | Ehrenkranz | |
| 4,443,851 A | 4/1984 | Lin | |
| 4,450,239 A | 5/1984 | Chatterton | |
| 4,465,077 A | 8/1984 | Schneider | |
| 4,466,445 A | 8/1984 | Abrams | |
| 4,475,158 A | 10/1984 | Elias | |
| 4,488,560 A | 12/1984 | Takamura | |
| 4,498,481 A | 2/1985 | Lemke | |
| 4,530,366 A | 7/1985 | Nessi et al. | |
| 4,534,362 A | 8/1985 | Schumacher et al. | |
| 4,557,273 A | 12/1985 | Stoller et al. | |
| 4,614,715 A | 9/1986 | Tsibris et al. | |
| 4,670,401 A | 6/1987 | Cutler et al. | |
| 4,676,254 A | 6/1987 | Frohn | |
| 4,685,471 A | 8/1987 | Reges et al. | |
| 4,691,714 A | 9/1987 | Wong et al. | |
| 4,752,880 A | 6/1988 | Aeschlimann | |
| 4,753,247 A | 6/1988 | Kirsner | |
| 4,770,186 A | 9/1988 | Regas et al. | |
| 4,779,627 A | 10/1988 | Kosasky | |
| 4,788,984 A | * 12/1988 | Marsik | 128/738 |
| 4,921,808 A | 5/1990 | Schneyer et al. | |
| 5,043,888 A | 8/1991 | Uriarte | |
| 5,050,612 A | 9/1991 | Matsumura | |
| 5,063,903 A | 11/1991 | Nucci | |
| 5,091,170 A | 2/1992 | Navot | |
| 5,137,028 A | 8/1992 | Nishimura | |
| 5,209,238 A | 5/1993 | Sundhar | |
| 5,216,599 A | 6/1993 | Uebe et al. | |
| 5,248,593 A | 9/1993 | Hubner-Parajsz et al. | |
| 5,657,762 A | * 8/1997 | Coley et al. | 600/548 |

FOREIGN PATENT DOCUMENTS

| | | |
|---|---|---|
| DE | 28 03 152 | 7/1979 |
| DE | 28 47 397 | 5/1980 |
| DE | 3 037 977 | 5/1982 |
| DE | 3 221 999 | 4/1983 |
| DE | 3 247 750 | 6/1984 |
| DE | 3 314 442 | 11/1984 |
| DE | 3 325 598 | 1/1985 |
| DE | 3 342 251 | 5/1985 |
| DE | 3 343 020 | 6/1985 |
| DE | 3 528 964 | 2/1987 |
| DE | 3 609 956 | 10/1987 |
| DE | 3 802 479 | 8/1989 |
| EP | 0 097 851 | 6/1983 |
| EP | 0 132 199 | 7/1984 |
| EP | 0 011 594 | 12/1984 |
| EP | 0 195 207 | 1/1986 |
| EP | 0 225 054 | 10/1986 |
| EP | 0 286 743 | 4/1987 |
| EP | 0 339 092 | 12/1987 |
| EP | 0 291 194 | 4/1988 |
| EP | 0 367 615 | 11/1989 |
| EP | 0 177 994 | 1/1990 |
| EP | 0 383 619 | 2/1990 |
| EP | 0 385 621 | 2/1990 |
| EP | 0 424 102 | 10/1990 |
| EP | 0 470 507 | 8/1991 |
| EP | 0 476 703 | 9/1991 |
| EP | 0 498 303 | 1/1992 |
| EP | 0 653 625 | 11/1994 |
| FR | 2 290 876 | 6/1976 |
| FR | 2 652 092 | 3/1991 |
| GB | 945670 | 1/1964 |
| GB | 1 203 619 | 8/1970 |
| GB | 2 045 480 | 10/1980 |
| GB | 2 106 646 | 4/1983 |
| GB | 2 116 318 | 9/1983 |
| GB | 2 186 977 | 8/1987 |
| WO | WO 80/02800 | 3/1980 |
| WO | WO 87/02774 | 5/1987 |
| WO | WO 90/11521 | 10/1990 |
| WO | WO 91/15594 | 10/1991 |
| WO | WO 94/02850 | 2/1994 |
| WO | WO 94/04926 | 3/1994 |
| WO | WO 84/03381 | 8/1994 |
| WO | WO 95/16920 | 6/1995 |

OTHER PUBLICATIONS

Home Urinary Luteinizing Hormone Immunoassays: Clinical Applications: Gregory H. Corsan, M.D., et al., Fertility and Sterility; vol. 53, No. 4, Apr. 1990.

Ovulation Test Instructions Taken From Clearplan Ovulation Test 510(k), Mar. 1987.

WHO Task Force (1983) *Fertility and Sterility*, 40 (6), p 773–778: 'A prospective multicentre trial of the ovulation method of natural family planning. III. Characteristics of the menstrual cycle and of the fertile phase'.

WHO Task Force (1985) *Int J Fertil*, 30(3), p 18–30: 'A Prospective Multicentre Study to Develop Universal Immunochemical Tests for Predicting the Fertile Period in Women'.

Wright et al (1979) *Steroids*, 34(4), p 445–457: 'Urinary excretion of estrone glucosiduronate, 17beta–estradiol–17–glucosiduronate, and estriol–16alphaglucosiduronate. Significance of proportionate differences during the menstrual cycle. I. Probit analysis'.

Yong et al (1989) *Aust NZ J Obstet Gynecol*, 29, p 155–160: 'Simple Office Methods to Predict Ovulation: The Clinical Usefulness of a New Urine Luteinizing Hormone Kit Compared to Basal Body Temperature, Cervical Mucus and Ultrasound'.

Zinaman et al (1989) *Biology of Reproduction*, 41, p 790–797: 'The Physiology of Sperm Recovered from the Human Cervix: Acrosomal Status and Response to Inducers of the Acrosome Reaction'.

Royston (1991) *Statistics in Medicine*, 10, p 221–240: 'Identifying the Fertile Phase of the Human Menstrual Cycle'.

Schiphorst et al (1985) *Fertility and Sterility*, 44(3), p 328–334: 'An estrogen test to determine the times of potential fertility in women'.

Singh et al (1984) *Fertility and Sterility*, 41(2), p 210–217: 'Clinical validation of enzymeimmunoassay of human luteinizing hormone (hLH) in the detection of the preovulatory luteinizing (LH) surge in urine'.

Singh et al (1984) *Hormone Receptors in Growth and Reproduction*, ed Saxena et al, Raven Press, NY, p 341–350: 'Clinical Validation of Enzyme Immunoassay for the Detection of the Preovulatory Luteinizing Hormone Surge in Urine'.

Stanczyk et al (1980) *Am J Obstet Gynecol*, 137(4), p 443–450: 'Direct radioimmunoassay of urinary estrogen and pregnanediol glucuronides during the menstrual cycle'.

*The Economist*, Mar. 23, 1991, p 128–129: 'Fertility: Keeping the beat'.

Tsibris et al (1989) *Int J Gynecol Obstet*, Suppl 1, p 73–82: 'Cervical mucus enzymes as markers of the woman's fertile period'.

Vermesh et al (1987) *Fertility and Sterility*, 47(2), p 259–264: 'Monitoring techniques to—predict and detect ovulation'.

Weerasekera et al (1983) *J Steroid Biochem*, 18(4), p 465–470: 'Multiple Immunoassay: The Simultaneous Measurement of Two Urinary Steroid Glucuronides as an Index of Ovarian Function'.

WHO Task Force (1980) *Am J Obstet Gynecol*, 138(4), p 383–390: 'Temporal relationships between ovulation and defined changes in the concentration of plasma estradiol–17beta, luteinizing hormone, follicle–stimulating hormone, and progesterone'.

WHO Task Force (1981) *Am J Gynecol Obstet*, 139(8), p 886–895: 'Temporal relationships between ovulation and defined changes in the concentration of plasma estradiol–17beta, luteinizing hormone, follicle–stimulating hormone, and progesterone. II. Histologic dating'.

WHO Task Force (1983) *Fertility and Sterility*, 39(5), p 647–655: 'Temporal relationships between indices of the fertile period'.

Lauzon et al (1992) *J Steroid Biochem Molec Biol*, 42(2), p 223–228: 'A Direct Dot–Enzyme Immunoassay to Detect Human Ovulation'.

Lewis et al (1993) *New Zealand Medical Journal*, Apr. 28, 1993, p 165–166: 'Recycling ovulation markers'.

Lewis et al (1994) *Steroids*, 59, p 288–291: 'Re–examining steroid hormone metabolites as ovulation markers using monoclonal antibodies'.

Landgren et al (1980) *Acta Endocrinologica*, 94, p 89–98: 'Hormonal profile of the cycle in 68 normally menstruating women'.

May (1989) *Proceedings of "Biotec '89" Conference*, Blenheim Online Publications, p 291–295: 'Clearblue One Step: adapting technology to the needs of the consumer'.

Moghissi et al (1972) *Am J Obstet Gynecol*, 114(3), p 405–418: 'A Composite picture of the menstrual cycle'.

Moghissi (1980) *Fertility and Sterility*, 34(2), p 89–98: 'Prediction and Detection of Ovulation'.

Moghissi (1992) *Reproductive Endocrinology*, 21(1) p 39–55: 'Ovulation Detection'.

Munro et al (1991) *Clin Chem*, 37 (6), p 838–844: 'Relationship of Serum Estradiol and Progesterone Concentrations to the Excretion Profiles of Their Major Urinary Metabolites as Measured by Enzyme Immunoassay and Radioimmunoassay'.

Paz et al (1990) *Gynecol Obstet Invest*, 29, p 207–210: 'Determination of Urinary Luteinizing Hormone for Prediction of Ovulation'.

*Population Reports*, Series 1, No. 3, Sep. 1991, p 1–33–1–71: 'Periodic Abstinence: How well do new approaches work?'.

Royston (1982) *Biometrics*, 38, p 397–406: 'Basal Body Temperature, Ovulation and the Risk of Conception, with Special Reference to the Lifetimes of Sperm and Egg'.

Fabres et al (1993) *Human Reproduction*, 8, p 208–210: 'Validation of the dual analyze assay of the oestrone:pregnanediol ratio in monitoring ovarian function'.

Flynn (1989) *Int J Gynecol Obstet*, Suppl 1, p 123–127: 'Natural family planning and the new technologies'.

Fordney–Settlage (1981) *Int J Fertil*, 26, p 161–169: 'A Review of Cervical Mucus and Sperm Interactions in Humans'.

France et al (1975) *J Reprod Fert*, Suppl 22, p 107–120: 'The Detection of Ovulation in Humans and its Applications in Contraception'.

Garcia et al (1981) *Fertility and Sterility*, 36(3), p 308–315: 'Prediction of the Time of Ovulation'.

Gudgeon et al (1989) *The Medical Journal of Australia*, 152, p 344, 346 and 349: 'Evaluation of the accuracy of the home ovulation detection kit, Clearplan, at predicting ovulation'.

Hatcher et al (1994) *Contraceptive Technology*, 16th Revised Edn, Irvington Publishers, NY, p 327–340: 'Fertility Awareness'.

Ismail et al (1989) *Contraception*, 39(1), p 53–71: 'An evaluation of the Bioself 110 fertility indicator'.

Judge et al (1978) *Steroids*, 31(2), p 175–187: 'Time–Course Relationships between Serum LH, Serum Progesterone and Urinary Pregnanediol Concentrations in Normal Women'.

Katz et al (1991) *Journal of Andrology*, Jan./Feb. 1991, Abstract 29: 'Human Cervical Mucus Properties and Sperm Mucus Interection during the Proliferative Phase of the Menstrual Cycle'.

Katz (1991) *Am J Obstet Gynecol*, 165(6), Part 2, p 1984–1986: 'Human cervical mucus: Research update'.

Kerin et al (1981) *British J Obstet Gynecol*, 88(2), p 81–90: 'Morphological and Functional Relations of Graafian Follicle Growth to Ovulation in Women Using Ultrasonic, Laparoscopic and Biochemical Measurements'.

Collins et al., "Biochemical Indices of the fertile period in women", Int J Fertil, 1981, 26(3), pp 196–202.

Collins et al., "Ovulation prediction and detection by the measurement of steroid glucuronides", Proc X Int Congress on Fertility and Sterility, 1981, pp 19–33.

Collines et al., "Biochemical methods for predicting ovulation", Fertility and Sterility, 1984, pp 59–69.

Collins, "Hormonal indices of ovulation and the fertile period", Adv Contracept, 1985, 1, pp 279–294.

Collines, "Biochemical Indices of potential fertility", Int J Gynecol Obstet, 1989, Supl. 1, pp 35–43.

Collins et al., "Ovarian morphology, endocrine function and intra–follicular blood flow during the peri–ovulatory period", Human Reproduction, 1991, 6(3), pp 319–324.

Collins (1991) *Am J Obstet Gynecol*, 165(6), p 1994–1996: 'The ecolution of reference methods to monitor ovulation'.

Collins (1992) *Biochem Soc Trans*, 20, p 234–237: 'Immunochemical tests of potential fertlity'.

Colombo (1989) *Int J Gynecol Obstet*, Suppl 1, p 13–18: 'Biometrical research on some parameters of the menstrual cycle'.

Corsan et al *Fertility and Sterility*, (1990) 53(4), p 591–601: 'Home urinary luteinizing hormone immunoassays: clinical applications'.

Denari et al (1981) *Obstetrics & Gynecology*, 58 (1), p 5–9: 'Determination of Ovarian Function Using First Morning Urine Steroid Assays'.

Djerassi (1990) *Science,* Jun. 1, 1990, p 1061–1062: 'Fertility Awareness: Jet–Age Rhythm Method?'.

Burger, "The physiologica basis of the fertile period", Fertility and Sterility, Eds. Harrison et al., MTP Press, 1984, pp. 51–58.

Burger, Estradiol: the physiological basis of the fertile period:, Int. J. Gynecol Obstet, Suppl 1, 1989, pp 5–9.

Campbell, "Methods of monitoring ovarian function and predicting ovulation: summary of a meeting", Research Frontiers in Fertility Regulation, 1985, 3(5), pp 1–16.

Cardone et al., "Objective and subjective data for fertile period diagnosis in women: comparison of methods", Clin Exp Obst Gyn, XIX, 1992, 1, pp 15–24.

Cekan et al., "The prediction and/or detection of ovulation by means of urinary steroid assays", Contraception, 1986, 33(4), pp 327–345.

Collins et al., "The concentrations of urinary oestrone–3–glucuronide, LH and pregnanediol–3a–gluronide as indices of ovarian function", Acta Endocrinologica, 1979, 90, pp 336–347.

Bischof et al., "Comparison of a rapid, quantitative and automated assay for urinary luteinizing hormone (LH), with an LH detection test, for the prediction of ovulation", Human Reproduction, 1991, 6(4), pp 515–518.

Bonnar, "Biological methods of identifying the fertile period", Fertility and Sterility, 1984, Eds. Harrison et al., MTP Press, pp 77–92.

Brown et al., "Appendix 1: Correlations between the mucus symptoms and the hormone markers of fertility throughout reproductive life", The Ovulation Method, $7^{th}$ Ed., Ed. Billings, Advocate Press, Melbourne, 1983, pp 99–125.

Brown et al., "Natural Family Planning", Am. J. Obstet. Gynecol, 1987, 157(4), Part 2, pp 1082–1089.

Brown et al., "Chemical and homogeneous immunoassay methods for the measurement of estrogens and pregnanediol and their glucuronides in urine", Non–Radiometric Assays: Technology and Application in Polypeptide and Steroid Hormone Detection, Publ. Alan R. Liss Inc., 1988, pp 119–138.

Brown et al., "New assays for identifying the fertile period", , Int. J. Gynecol Obsted, Suppl. 1, 1989, pp 111–122.

Adlercreutz et al., "Prediction of ovulation by urinary estrogen assays", J. Steroid Biochem, 1980, v. 12, pp 395–348.

Adlercreutz et al., "The measurement of urinary sterioid glucuronides as indices of the fertile period in women", J. Steroid Biochem, 1982, v. 17, pp 695,702.

Albertson et al., "Review Article: The prediction of ovulation and monitoring of the fertile period", Adv. Contracept, v. 3, pp 263–290.

Baird et al., "Using the ratio of urinary oestrogena nd progesterone metabolites to estimate day of ovulation", Statistics in Medicine, 1991, 10, pp 255–266.

Barnard et al., "A nonseparation, time–resolved fluoroimmunoassay to minitor ovarian function and predict potential fertility in women", Fertility and Sterility, 1989, 52(1), pp 60–65.

Bieglmayer et al., "Evaluation of a simple and fast self–test for urine luteinizing hormone", Fertility and Sterility, 1990, 53(5), pp 842–846.

* cited by examiner

ADVISORY METHOD

This is a continuation of application Ser. No. 08/458,184, filed on Jun. 2, 1995, which was abandoned upon the filing hereof, which was a continuation of application Ser. No. 08/109,502, filed Aug. 20, 1993, and now abandoned.

This invention relates to methods and devices enabling contraceptive advice to be provided during the human ovulation cycle.

Devices are already commercially available which purport to provide the user with contraceptive advice. Generally these are based on the measurement of basal body temperature, and require the user to make daily measurements. The reliability of the contraceptive advice provided by such devices is questionable.

Devices are also available which measure the concentration of urinary lutenising hormone (LH), and alert the user to the LH surge indicative of ovulation, as an aid to conception.

Although the absolute urinary concentration value of LH varies from one individual to another, and from one cycle to another, the LH surge is such a pronounced event that for practical purposes a urinary LH concentration of 20 mIU/ml can be regarded as a universal threshold indicative of the LH surge under virtually all circumstances.

Although the LH surge is a clearly measurable event, it has not hitherto been regarded as an acceptable indicator for contraceptive purposes because it occurs such a short while prior to actual ovulation. Practical contraceptive advice, which would allow a user to avoid conception by abstaining from unprotected intercourse (ie. without resort to any physical or hormonal contraceptive technique) for a minimal portion of the normal ovulation cycle, has not been considered possible if based solely on the measurement of urinary LH concentration.

The expression "LH surge" is used herein to mean the dramatic rise in LH concentration that precedes the event of ovulation. In the art, reference is made also to "LH max", i.e. the peak concentration of LH. In the majority of individuals, these are for all practical purposes simultaneous, when the cycle is monitored on a day-by-day basis. However, in a few individuals, perhaps 20% of the population, the actual peak concentration of LH is not observed until the day following the main concentration rise. For the purposes of the invention, we prefer to use the observable rise as the critical parameter.

By the invention we have found that, contrary to such expectation, reliable contraceptive advice can be derived simply from the measurement of urinary LH concentration if such measurement is linked to a critical 'calender' provided for the user.

Previously proposed contraceptive methods based on urinary component analysis have tended to require extensive daily urine sampling and testing, often throughout the entire cycle. Other methods have tended to require an unduly prolonged period of abstinence from unprotected intercourse. The invention achieves a reasonable balance by enabling the testing period and abstinence period to be reduced while providing a worthwhile degree of certainty in the contraceptive advice to the user, and employs techniques that can readily be applied in the home.

The invention provides a method of reducing the likelihood of conception during the human ovulation cycle, wherein commencing on a predetermined day in the interval from numerical day 5 to numerical day 15 inclusive following the onset of menses, frequent (preferably daily) testing of urinary lutenising hormone (LH) concentration is performed until the LH surge associated with ovulation is detected, and unprotected intercourse is avoided during a time interval commencing on or before the first day of urinary LH concentration testing and ending at least 2 days, preferably at least 3 days, following the day of LH surge detection.

The predetermined day on which LH testing should be started can be indicated to the user in instructions associated with an appropriate test kit. The starting day should be sufficiently in advance of a likely ovulation day in a typical cycle, to provide a reasonable "safe" period during initial use of the method of the invention.

Preferably, at least during an initial usage cycle, commencement of testing is begun not more than 8 days, more preferably not more than 7 days, following the onset of menses.

Preferably, at least during an initial usage cycle, avoidance of unprotected intercourse is begun not more than 8 days, more preferably not more than 7 days, following the onset of menses.

The invention also provides a test kit for providing awareness of the status of the human ovulation cycle, comprising a plurality of disposable urinary LH concentration testing devices together with means enabling a user to record the results of frequent (eg. daily) urinary LH tests and to alert the user to the likelihood of conception occurring, characterised in that the recording/alerting means (and/or instructions associated therewith) advises the user to commence testing on a predetermined day in the time interval from numerical day 5 to numerical day inclusive 15 following the onset of menses and to abstain after the predetermined day from unprotected intercourse until at least 2 days have elapsed following the day of detection of the LH surge.

Preferably, the recording/alerting means (and/or instructions associated therewith) advises the user to commence testing in the subsequent cycle on a numerical day that is at least 4 but not more than 8 days in advance of the numerical day corresponding to the day of detected LH surge in the current cycle. Preferably, the user is advised to abstain from unprotected intercourse until at least 3 days have elapsed following the detection of the LH surge.

The recording\alerting means can, for example, be a chart on which the user enters the results of the daily testing, commencing on a predetermined day following the onset of menses. If desired, the chart can be provided with a slidable overlay or cursor indicating an appropriate time interval in accordance with the invention, incorporating for example a marker that the user can locate adjacent on an identified day of LH surge and which can then indicate the end of the "unsafe" interval. As a preferred feature, the cursor can enable the user to adapt the method of the invention to modify and preferably reduce the number of test days in the subsequent cycle. This can be achieved if the cursor accommodates means to advise the user of an optimum test starting day to be used in the subsequent cycle in advance of the expected day of LH surge detection. In order to provide an adequate "safe" interval and to accommodate normal variations that are likely to occur between one cycle and another in the same individual, the revised test starting day should be set as a defined number of days in advance of the day of observed LH surge in the current cycle.

Preferably, the recording chart on which daily urinary LH concentrations can be recorded during the course of an ovulation cycle is provided with a cursor that can highlight a group of consecutive "days" on the chart and which cursor, by alignment with a "day" on which the LH surge detection is recorded, can advise the user of the residual unsafe period during the current cycle. More preferably, the cursor can advise the user to commence urinary LH concentration testing on a predetermined numerical day in the subsequent cycle during the interval of at least 4 but not more than 8 days inclusive in advance of the numerical day of LH surge detection in the current cycle.

The chart can be made re-useable, but preferably is disposable and a new chart is supplied with a plurality of assay devices sufficient for testing during a single cycle.

Alternatively, the recording/alerting means can be an electronic device, such as an electronic monitor, e.g. a micro-processor controlled device, into which the daily test results are entered, e.g. by means of an automatic reader of a sampling device, and which can calculate the calender for the user.

Another aspect of the invention is a disposable urinary LH concentration testing advice when used as part of a test kit as defined above, comprising a reagent-impregnated immunochromatographic assay strip incorporating an anti-LH antibody labelled with a particulate direct label, such as a dye sol, gold sol, or coloured latex particles, the device having a urinary LH concentration sensitivity sufficient to provide to the user a clear test result indicative of the onset of the LH surge. Preferably the assay sensitivity is such that a clear indication is given to the user when the urinary LH concentration rises to a level in the range 20–30 mIU/ml. Suitable testing devices are described in detail in patent specifications GB-A-2204398 and EP-A-383619, the disclosures of which are incorporated herein by reference.

The selection of the appropriate calender is critical to the success of the invention. If commencement of LH testing is too early, an unduly prolonged period of abstinence from unprotected intercourse will be recommended to the user and an essential objective of the invention will be negated. Following identification of the LH surge, the user should be advised promptly of the resumption of the 'safe' period.

Although there is much reported experimental work in the scientific literature on the changing urinary hormone metabolite profiles during the human ovulation cycle, we believe that the present invention constitutes the first practical use of a knowledge of the LH profile alone adapted to a simple but constructive means for alerting the user to the status of her current ovulation cycle for the primary purpose of contraception, and which is sufficiently reliable for home use. The literature does not suggest the LH measurement alone could provide sufficiently reliable contraceptive advice, especially under home-use circumstances. Rather, the thinking in the art has been that multiple factors need to be measured and correlated to provide reliable contraceptive advice, even under sophisticated laboratory circumstances.

By way of example only, practical aspects of the invention are described below with reference to the accompanying drawings.

FIGS. 1, 2 and 3 of the accompanying drawings illustrate assay result recording means which can be used in accordance with the invention:

Figure 1:
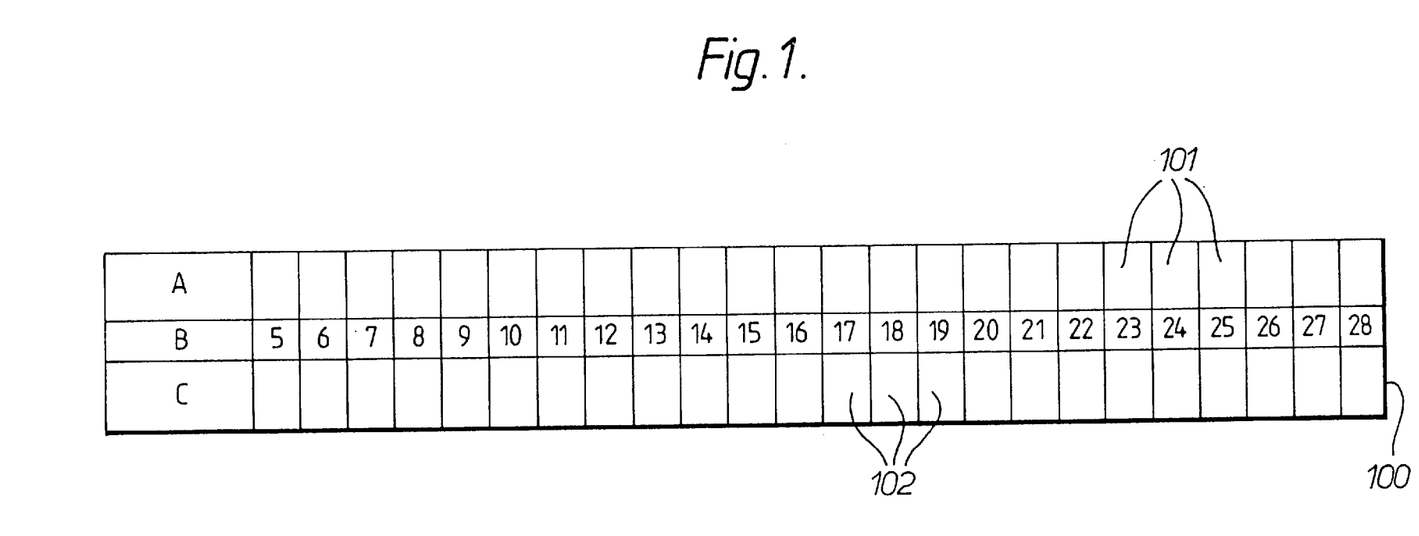
FIG. 1 shows a simple chart on which the result of daily LH concentration assays can be recorded.

Referring to FIG. 1, the chart comprises an elongated strip 100 of stout paper or similar material incorporating separate spaces for consecutive cycle days running (arbitrarily) from day 5 to day 28. Above an indication of each numerical day is a space 101 in which an assay result can be indicated by the user. Below the indication of each numerical day is a space 102 in which (if desired) the user can enter the actual date or other relevant information. Spaces A, B and C on the left hand end of the chart as illustrated, can contain instructions to the user. For the purpose of example, it can be assumed that the standard instructions to the user are to commence daily urinary LH testing on numerical day 7. The day of LH surge detection is likely to be in the interval from numerical day 12 to numerical day 20, in normal individuals.

Figure 2A:
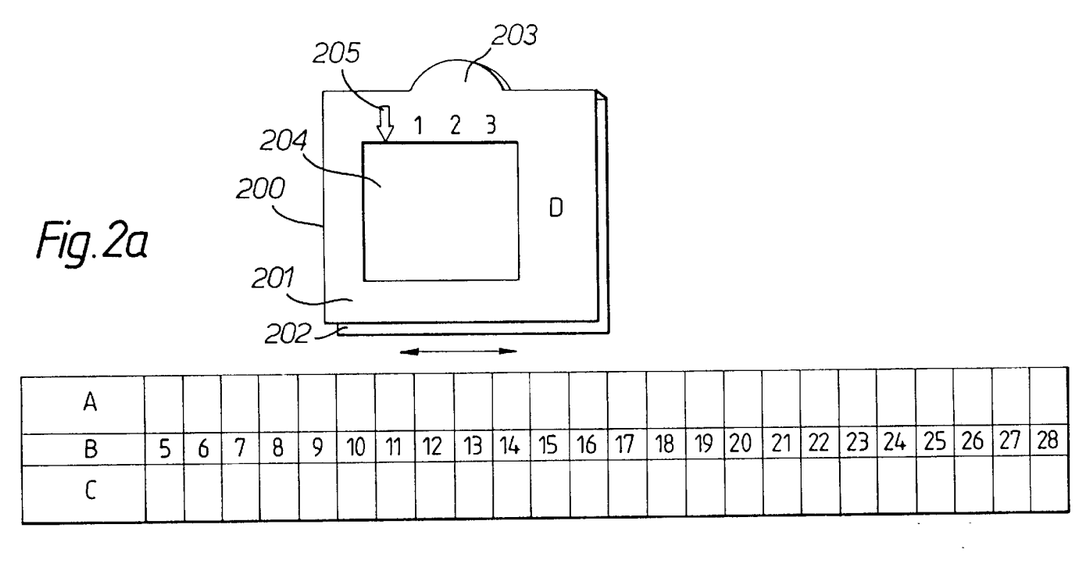
FIG. 2*a* shows the same chart, together with a cursor that can be run along the chart to aid the user in interpreting the results.

Referring to FIG. 2*a*, the cursor 200 comprises a simple "sandwich" structure having a front face 201 and a rear face 202 linked at the top, with a handle extension 203 by means of which the user can hold the cursor. The front face of the cursor incorporates a window 204 so that when the cursor is slipped over the chart a portion of the chart is visible through the window. Enlarged portion D of the front face of the cursor can accommodate further instructions to the user. When placed over the chart, the cursor can be slid by the user along the chart. The window is sufficient to expose four "days" of the chart at any one time. The left hand "day" is indicated by an arrow 205 on the cursor and the remaining days are identified as "1, 2 and 3".

In practice, the user should record the daily urinary LH concentration assay result on the chart in accordance with instructions associated with the assay kit, for example commencing daily LH testing on numerical day 7. On the day that the assay result indicates that the LH surge has commenced, the cursor should be moved along the chart so that the arrowed day is the present day. This will alert the user to the fact that the three immediately subsequent days (days "1, 2 and 3" on the cursor) constitute the end of the "unsafe" period and thereafter unprotected intercourse can be resumed until the next cycle.

Figure 3A:
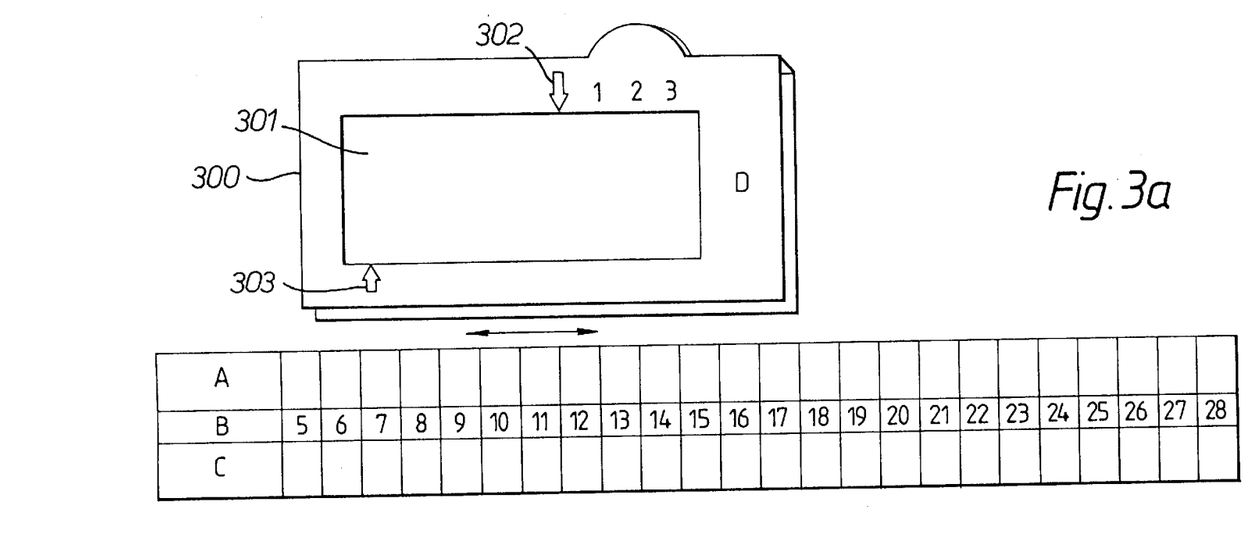
FIGS. 3*a* and 3*b* show a similar combination of chart and cursor as shown in FIGS. 2*a* and 2*b* except that the cursor of FIG. 3*a* incorporates means to advise the user of an appropriate test starting day in the following cycle.

Referring to FIG. 3*a*, the cursor 300 accommodates a larger window 301 which exposes a total of 9 "days" of the recording chart. The sixth "day" of the cursor window is the arrowed day 302 which the user should align with the actual day of LH surge observation during the current cycle. Thereafter the cursor indicates three further days which constitute the remainder of the "unsafe" period, as described in the previous paragraph.

The five "days" revealed by the cursor in advance of the LH surge day represent a reasonable testing period for use in the subsequent cycle. A further arrow 303 on the cursor is placed below the first of these five days.

Figure 3B:
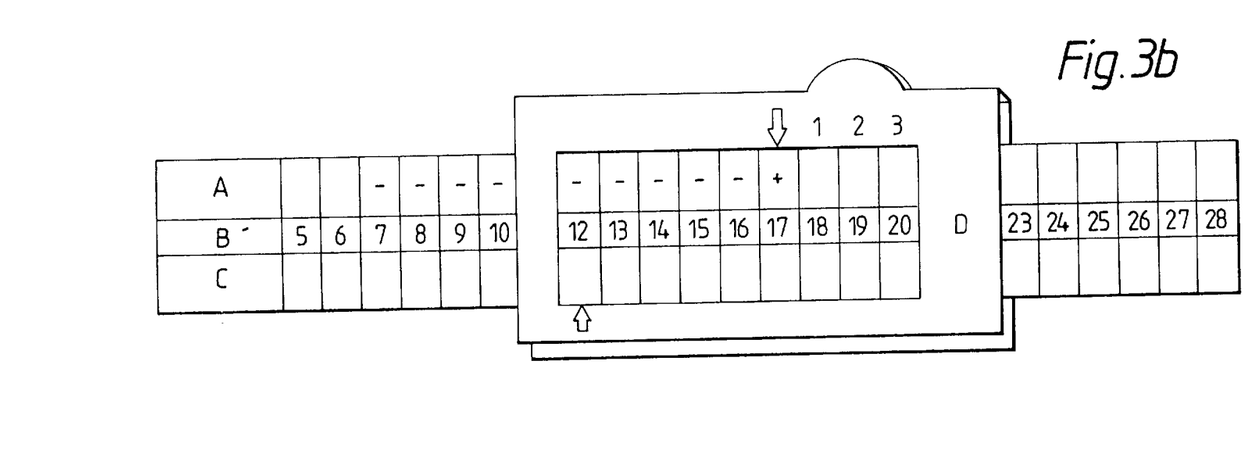

Referring to FIG. 3*b*, it is assumed for the purposes of example that LH surge in the current cycle has been identified on day 17 of the cycle. The cursor is seen on the recording chart with the LH surge day arrow 302 adjacent the entry for day 17. The arrowed day 303 at the left hand end of the cursor window is day 12 of the current cycle. The user can assume that in her next cycle she can commence daily LH concentration testing on numerical day 12 rather than day 7 in accordance with the basic instructions with the test. The number of LH concentration tests in the subsequent cycle is therefore reduced, and unprotected intercourse need not be avoided until day 12 of the subsequent cycle.

Figure 4:
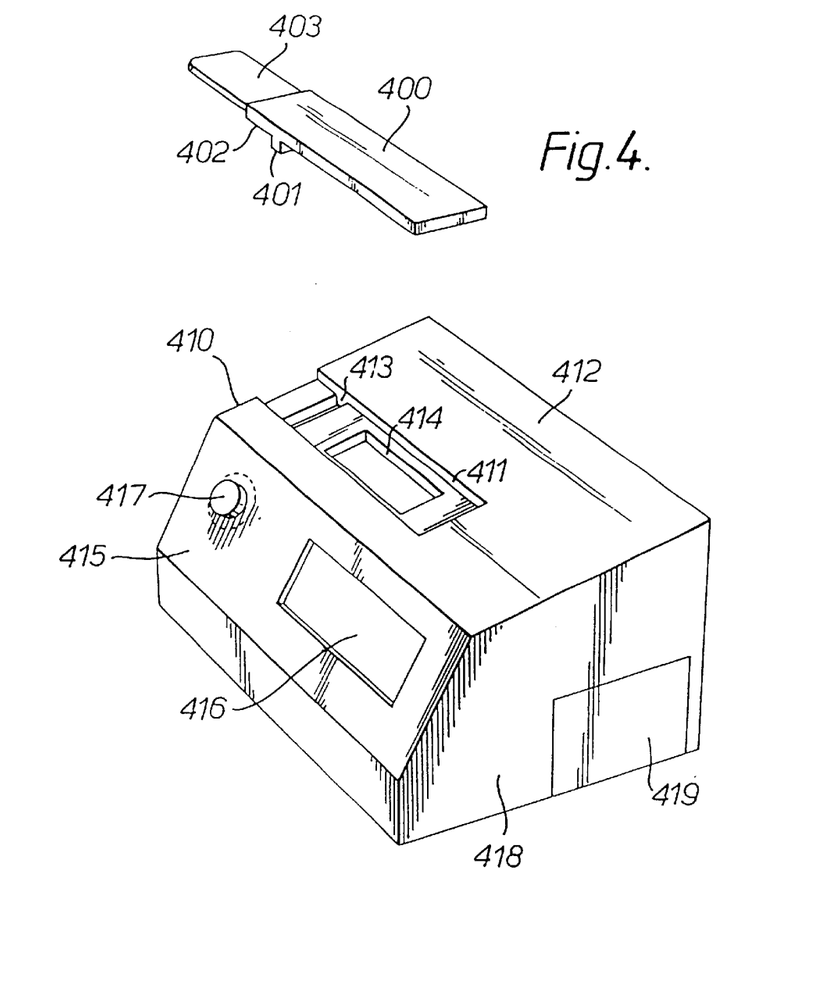
FIG. 4 of the accompanying drawings illustrates an ovulation cycle monitoring device for use in accordance with the invention, together with an associated urine sample testing device.

Referring to FIG. 4, the urine sample testing device comprises a flat elongate casing 400 having a locating ridge 401 on its lower surface 402. Projecting from one end of the casing is a bibulous sample receiving member 403.

The monitor comprises a casing 410 having a recess 411 in its upper surface 412 to accommodate the casing 400 of the testing device. Recess 411 incorporates a locating slot 413 into which the locating ridge 401 on the casing of the testing device can be inserted to positively locaate the testing device in relation to a reading window 414 in the recess. Casing 410 contains means (not shown) such as a fluorescence reader to measure the result of a urinary LH concentration assay performed using the testing device.

The sloping front face 415 of the monitor casing incorporates a large window 416 through which information can be conveyed to the user eg. by means of an LED display or other visual output. This information can be provided in a variety of forms, such as an indication of a calender and the need to perform urine tests, and an indication of the current status of the ovulation cycle. The sloping face 415 of the casing also incorporates a button 417 which the user can press to indicate the commencement of an ovulation cycle and to start the monitor processing information relative to that cycle.

In general the monitor will be battery-powered, and incorporates in side 418 of the casing an access point such as a removable cover 419 to permit batteries to be inserted and changed.

Figure 5:
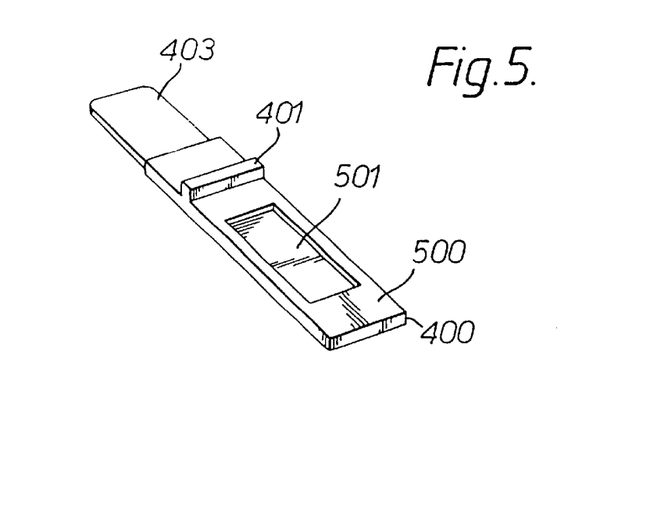
FIG. 5 shows the urine testing device in greater detail.

Referring to FIG. 5, the testing device is shown inverted relative to the aspect seen in FIG. 1. The locaating ridge 401 is now on the upper surface 500. Also in the surface 500 now uppermost is a result window 501. The body of the testing device can incorporate an immunochromatographic strip (not shown) incorporating all necessary reagents to enable an immunoassay to be formed which detects the presence and concentration of LH in a urine sample applied to the sample collecting member 403. The result of the assay can be effected by the immobilization of a labelled component, via a sandwich or competition reaction in the presence of LH in an applied urine sample, the labelled reagent becoming concentrated in a zone revealed through the result window. When the testing device is inverted and located in the recess 411 in the casing of the monitor, the result window is immediately adjacent to the reading window 414 in the monitor and the assay result can be determined. For example, if the label is a fluorescent reagent, the reading means within the monitor can detect and measure fluorescent light output from the accumulated label in the detection zone on the strip to provide a numerically accurate concentration value for the LH in the urine sample. This information can be processed by the monitor together with calender information resulting from the initiation of the cycle process by the user and historical data which the monitor can retain from previous cycles.

Figure 6:
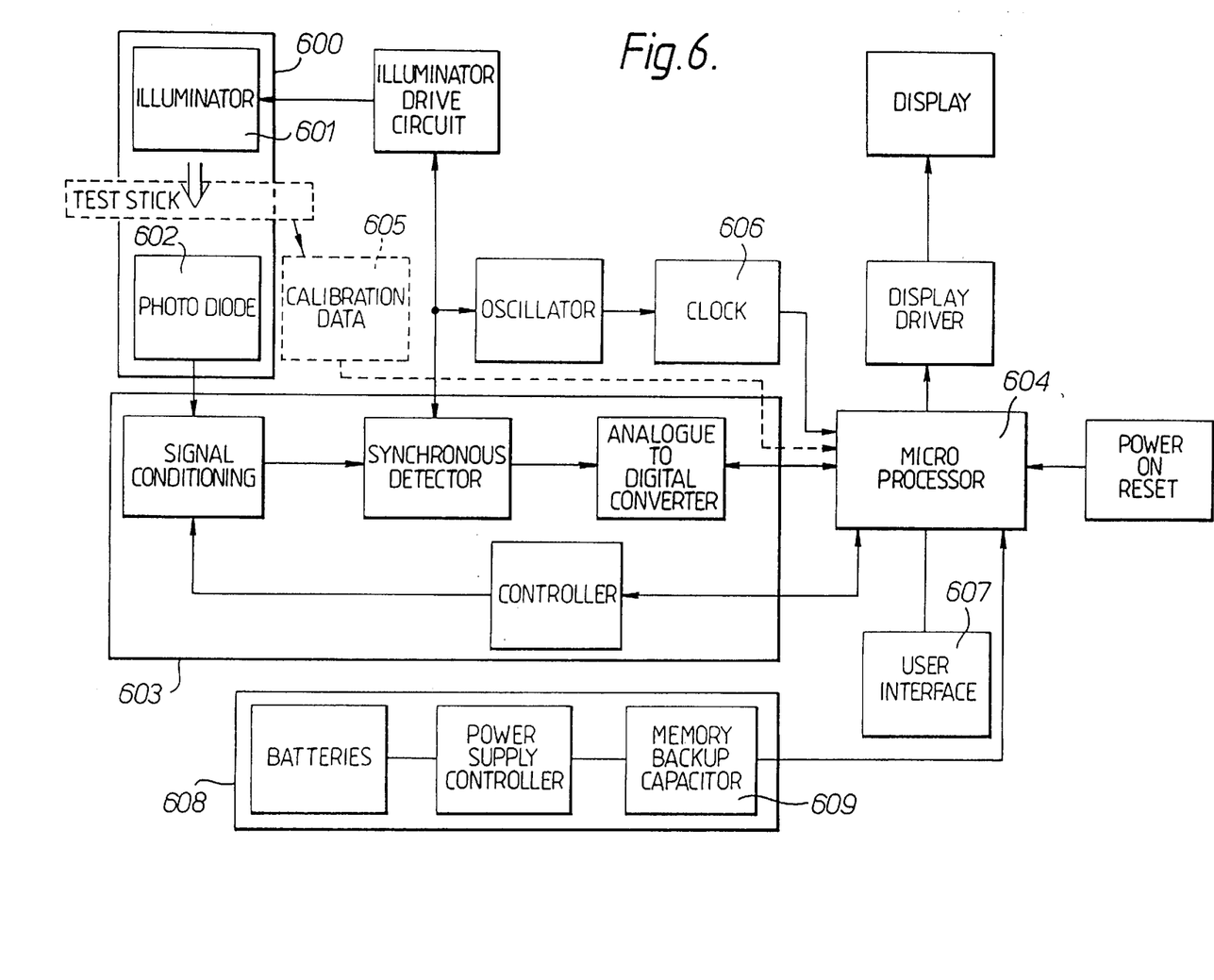
FIG. 6 shows, in schematic form, the basic functions that may be required in an electronic monitor for use in accordance with the invention.

Referring to FIG. 6, some of the basic elements which may be required in an electronic monitoring device are seen. The individual features can be entirely conventional, and those familiar with the art of electronics will appreciate that other combinations and arrangements of such features can be employed to achieve the objectives of the invention. For example, so-called "hard-wired" systems, and "neural networks", can be used in place of conventional microprocessors based on "chip" technology. As depicted in FIG. 6, the combination essentially comprises:

A reading unit 600 to derive information from a test device, such as a test stick, the leading unit comprising an illuminator 601 and a reader 602 (represented here as a photo diode). The leading unit feeds into a conversion unit 603 to convert the optical signal into a form usable by a microprocessor 604. As an optional feature, a calibration system 605 is provided to convert the signal derived from the reading unit into data corresponding, for example, to an absolute concentration value. A timer, such as a clock 606 is required to regulate measurements within a cycle. The microprocessor 604 processes, memorizes and interprets results in the light of previous events, particularly recorded from previous cycles. The user interface 607 will generally comprise at least means, such as a push button, which the user can operate at the commencement of a cycle to initiate the operation of the device as a whole. The power supply 608 should include means, such as a memory back up capacitator 609, to prevent loss of historical data if it becomes necessary to replace batteries.

The following Examples illustrates how reliable practical contraceptive advice can be provided by means of the invention.

EXAMPLE 1

A plurality of urinary LH concentration assay devices, essentially constructed as described in Embodiment 3 and illustrated in FIGS. 8 to 10 of UK patent specification GB 2204398B, are used in conjunction with a recording chart as shown in FIG. 1 of the accompanying drawings. In essence, each assay device comprises an immunochromatographic assay strip within a plastics casing, incorporating a mobile anti-LH antibody labelled with blue-coloured polystyrene (latex) microparticles, and having an assay result zone on the strip bearing an immobilised unlabelled anti-LH antibody capable of forming a sandwich complex in the presence of LH to provide a readily visible result in the form of a blue line appearing in a window in the casing when the LH concentration in an applied urine sample exceeds 20 mIU/ml. Daily urinary LH assays are conducted, commencing on day 7 of a human ovulation cycle (calculated as the seventh day following the onset of menses), and the day of occurrence of the LH surge is noted. Unprotected intercourse is avoided during the interval from day 7 until the third day, inclusive, following the day of occurrence of the LH surge. Conception does not occur.

EXAMPLE 2

A study was conducted with two individuals. Early morning urine samples were tested with an LH assay device as described in Example 1, and the same samples were tested in the laboratory for P3G concentration with a quantitative enzyme immunoassay. The purpose of the P3G assay was to validate the conclusions drawn from the LH positive results. Thus, a positive LH result implies that the luteal infertile phase will begin in 2–3 days time, the ovum having irreversibly passed through the uterus. If this conclusion is correct, then at least the start of a sustained rise in P3G should be detectable 3 days after the first positive LH result, as it is known that the luteal phase can be defined by the rise in blood progesterone.

The tables of results show data from 3 cycles of each volunteer. Column 1 (day of cycle) shows the day of testing, relative to the onset of menses. The first observation in each set is that obtained four days before the first positive LH result, to show the range of background (or non-elevated) P3G values, above which a rise can be detected.

Figure 2B:
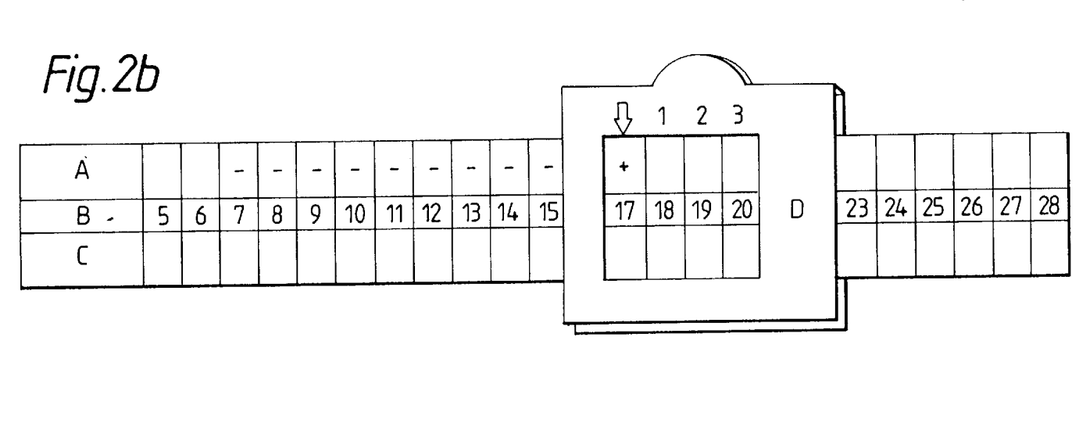
FIG. 2*b* shows the cursor in place on the chart during a typical assay interpretation.

The final column relates the actual results to the advice that a user would receive if employing a recording chart as illustrated in FIGS. 2a/b, based upon the timing of the LH positive result. LH results are simply expressed as positives or negatives, without any attempt to rank or deduce quantitative information. The first positive result is expressed in bold type, as this is taken as the key piece of information.

P3G concentrations are given for each day, but no attempt is made to define threshold values, as such values vary considerably from cycle to cycle. Cusum analysis could be used to identify the P3G rise, but in these studies, the onset of a sustained rise is clearly evident without the need for statistical treatments. For example, in cycle 1 of volunteer A, values of P3G approaching 3,500 ng/ml occur up to and including the first LH positive day. The values found on the "safe" days are all at least 60% higher than those observed before the positive LH result.

In every cycle from each volunteer there is a clear and unmistakable rise in P3G values coinciding with start of the infertile phase, as deduced from the LH results, so confirming the surprising accuracy of infertile phase prediction from urinary LH detection.

| Day of cycle | LH result | P3G conc (ng/ml) | Cursor "day" |
|---|---|---|---|
| INDIVIDUAL A Cycle 1 (30 days) | | | |
| 12 | − | 1435 | |
| 13 | − | 1666 | |
| 14 | − | 3222 | |
| 15 | − | 1012 | |
| 16 | + | 3369 | |
| 17 | + | 4510 | 1 |
| 18 | − | 3256 | 2 |
| 19 | − | 7052 | 3 |
| 20 | − | 5244 | Safe |
| 21 | − | 9944 | Safe |
| 22 | − | 9521 | Safe |
| Cycle 2 (28 days) | | | |
| 11 | − | 689 | |
| 12 | − | 1235 | |
| 13 | − | 873 | |
| 14 | − | 2477 | |
| 15 | + | 2838 | |
| 16 | + | 3237 | 1 |
| 17 | − | 5522 | 2 |
| 18 | − | 8578 | 3 |
| 19 | − | 13309 | Safe |
| 20 | − | 5658 | Safe |
| 21 | − | 8622 | Safe |
| Cycle 3 (29 days) | | | |
| 11 | − | 1714 | |
| 12 | − | 864 | |
| 13 | − | 1518 | |
| 14 | − | 1818 | |
| 15 | + | 2249 | |
| 16 | + | 1388 | 1 |
| 17 | − | 2057 | 2 |
| 18 | − | 5404 | 3 |
| 19 | − | 6756 | Safe |
| 20 | − | 9147 | Safe |
| 21 | − | 8723 | Safe |
| INDIVIDUAL B Cycle 1 (31 days) | | | |
| 14 | − | 494 | |
| 15 | − | 776 | |
| 16 | − | 315 | |
| 17 | − | 540 | |
| 18 | + | 554 | |
| 19 | − | 1081 | 1 |
| 20 | − | 3498 | 2 |
| 21 | − | 2489 | 3 |
| 22 | − | 3316 | Safe |
| 23 | − | 6085 | Safe |
| 24 | − | 4562 | Safe |
| Cycle 2 (24 days) | | | |
| 12 | − | 1505 | |
| 13 | − | 1379 | |
| 14 | − | 615 | |
| 15 | − | 1567 | |
| 16 | + | 841 | |
| 17 | − | 1493 | 1 |
| 18 | − | 800 | 2 |
| 19 | − | 1785 | 3 |
| 20 | − | 5414 | Safe |
| 21 | − | 8053 | Safe |
| 22 | − | 7446 | Safe |
| Cycle 3 (35 days) | | | |
| 18 | − | 746 | |
| 19 | − | 456 | |
| 20 | − | 716 | |
| 21 | − | 500 | |
| 22 | + | 775 | |
| 23 | + | 600 | 1 |
| 24 | − | 1864 | 2 |
| 25 | − | 2618 | 3 |
| 26 | − | 3183 | Safe |
| 27 | − | 5601 | Safe |
| 28 | − | 7327 | Safe |

What is claimed is:

1. A method of reducing the likelihood of conception during the human ovulation cycle by requiring the measurement of only urinary lutenising hormone (LH) concentration, which comprises, commencing on a predetermined day in the interval from numerical day 5 to numerical day 15 inclusive following the onset of menses, and at least 4 but not more than 8 days in advance of the numerical day corresponding to the day of detected LH surge in a previous cycle, performing frequent repeated daily testing of only urinary LH concentration until the LH surge associated with ovulation is detected, and avoiding unprotected intercourse during a time interval commencing on or before the first day of said repeated daily urinary LH concentration testing and ending at least 2 days following the day of LH surge detection.

2. A method according to claim 1, wherein at least during an initial usage cycle, commencement of testing, and avoidance of unprotected intercourse, are both begun not more than 7 numerical days following the onset of menses.

3. A method according to claim 1 or claim 2, wherein unprotected intercourse is avoided during a time interval ending at least 3 days following the day of LH surge detection.

4. A method according to claim 1, wherein the predetermined day on which testing is commenced is determined based upon the numerical day corresponding to the day of detected LH surge in the immediately previous cycle.

5. A plurality of disposable urinary LH assay devices having a sensitivity such that a user thereof can be alerted to the occurance of the LH surge, packaged together with instruction for use in a method according to claim 1.

6. A test kit for providing awareness of the status of the human ovulation cycle, simply comprising a plurality of disposable urinary LH concentration testing devices together with recording/alerting means enabling a user to record the results of repeated daily urinary LH tests and to alert the user to the likelihood of conception occurring, characterized in that the recording/alerting means is adapted to advise the user to commence said repeated daily testing on a predetermined day in the time interval from numerical day 5 to numerical day 15 inclusive following the onset of menses and at least 4 but not more than 8 days in advance of the numerical day corresponding to the day of detected LH surge in a previous cycle and to abstain the predetermined day from unprotected intercourse until at least 2 days have elapsed following the day of detection of the LH surge.

7. A test kit according to claim 6, wherein the user is advised to abstain from unprotected intercourse until at least 3 days have elapsed following the detection of the LH surge.

8. A disposable urinary LH concentration testing device when used as part of a test kit according to claim 6, comprising a reagent-impregnated immunochromatographic assay strip incorporating an anti-LH antibody labelled with a particulate direct label, the assay strip having a urinary LH concentration sensitivity sufficient to provide to the user a test result indicative of the onset of the LH surge.

9. A device according to claim 8, wherein the urinary LH concentration sensitivity is such that an indication is given to the user when the urinary LH concentration rises to a level in the range 20–30 mIU/ml.

10. A test kit according to claim 6, wherein the recording means comprises a chart on which the user can enter daily urinary LH concentration test results.

11. A test kit according to claim 6, wherein the predetermined day on which testing is commenced is determined based upon the numerical day corresponding to the day of detected LH surge in the immediately previous cycle.

12. A test kit for providing awareness of the status of the human ovulation cycle, simply comprising a plurality of disposable urinary LH concentration testing devices together with recording/alerting means enabling a user to record the results of repeated daily urinary LH tests and to alert the user to the likelihood of conception occurring, characterized in that the recording/alerting means is adapted to advise the user to commence said repeated daily testing on a predetermined day in the time interval from numerical day 5 to numerical day 15 inclusive following the onset of menses and to abstain the predetermined day from unprotected intercourse until at least 2 days have elapsed following the day of detection of the LH surge, wherein the recording means comprises a chart on which the user can enter daily urinary LH concentration test results and wherein the chart is provided with a cursor that the user can position adjacent a "day" on the chart on which the LH surge detection is entered.

13. A test kit according to claim 9, wherein the cursor advises the user of an optimum test starting day in the subsequent cycle.

14. A recording chart on which daily urinary LH concentrations can be recorded during the course of an ovulation cycle, together with a cursor that can highlight a group of consecutive "days" on the chart and which cursor, by alignment with a "day" on which the LH surge detection is recorded, can advise the user of the residual unsafe period during the current cycle.

15. A recording chart and cursor combination according to claim 14, wherein the cursor can advise the user to commence urinary LH concentration testing on a predetermined numerical day in the subsequent cycle during the interval of at least 4 but not more than 8 days inclusive in advance of the numerical day in the subsequent cycle corresponding to the numerical day of LH surge detection in the current cycle.

* * * * *